United States Patent
Borsari et al.

(10) Patent No.: US 8,783,787 B2
(45) Date of Patent: Jul. 22, 2014

(54) HOMOGENEOUS CORE WIRE PROTECTIVE CLEANING TIP

(71) Applicants: Mark N. Borsari, East Granby, CT (US); David Hudson, East Granby, CT (US)

(72) Inventors: Mark N. Borsari, East Granby, CT (US); David Hudson, East Granby, CT (US)

(73) Assignee: Sanderson-Macleod, Inc., Palmer, MA (US)

( * ) Notice: Subject to any disclaimer, the term of this patent is extended or adjusted under 35 U.S.C. 154(b) by 0 days.

(21) Appl. No.: 13/787,140

(22) Filed: Mar. 6, 2013

(65) Prior Publication Data

US 2014/0021773 A1    Jan. 23, 2014

Related U.S. Application Data

(62) Division of application No. 12/697,637, filed on Feb. 1, 2010.

(60) Provisional application No. 61/149,034, filed on Feb. 2, 2009.

(51) Int. Cl.
*A46D 3/00* (2006.01)

(52) U.S. Cl.
USPC .................................................. 300/21

(58) Field of Classification Search
USPC ............................ 15/164, 206, 104.2; 300/21
See application file for complete search history.

(56) References Cited

U.S. PATENT DOCUMENTS

| | | | | | |
|---|---|---|---|---|---|
| 1,825,929 | A | * | 10/1931 | Voigt | 15/206 |
| 1,967,597 | A | * | 7/1934 | Schwartz | 15/206 |
| 2,633,592 | A | * | 4/1953 | Meyer | 15/206 |
| 3,582,140 | A | | 6/1971 | Kaufman | |
| 3,613,664 | A | * | 10/1971 | Willson et al. | 600/569 |
| 6,699,331 | B1 | * | 3/2004 | Kritzler | 134/8 |
| 2003/0084913 | A1 | | 5/2003 | Gueret | |
| 2005/0172437 | A1 | * | 8/2005 | Wachter | 15/179 |
| 2008/0034524 | A1 | | 2/2008 | Takahashi | |
| 2010/0319720 | A1 | * | 12/2010 | Thorne et al. | 132/218 |

FOREIGN PATENT DOCUMENTS

WO     02081108 A1    10/2002

* cited by examiner

*Primary Examiner* — Randall Chin
(74) *Attorney, Agent, or Firm* — McCormick, Paulding & Huber LLP

(57) ABSTRACT

A method of forming a protective tip on a wire brush so as to make the brush less prone to damage sensitive surfaces, includes the steps of providing a brush with a wire core and a plurality of bristles defining a bristle block extending radially from the core and anchored in the core, and melting a portion of the wire core at an end thereof, by applying an energy source to the end, to form a protective tip.

17 Claims, 4 Drawing Sheets

HOMOGENEOUS CORE WIRE PROTECTIVE CLEANING TIP

CROSS REFERENCE TO RELATED APPLICATIONS

This application is a divisional of U.S. patent application Ser. No. 12/697,637 filed on Feb. 1, 2010 now pending, which claims priority to, and the benefit of, U.S. Provisional Application Ser. No. 61/149,034, filed on Feb. 2, 2009, which are herein incorporated by reference in their entirety.

FIELD OF THE INVENTION

The present invention relates generally to mechanical abrasion cleaning technology, and, more particularly, to a cleaning apparatus having a protective tip that is less prone to scratch, scar or damage sensitive cleaning surfaces, and further to a device and a method of making the same.

BACKGROUND OF THE INVENTION

Brushes for cleaning the inner surfaces of vessels are well known in the art. One type of such brush is the twisted in wire brush, which is commonly used in a variety of applications including, but not limited to, hole cleaning, sanding, deburring or lubricating, tube or vessel cleaning, beaker cleaning, pistol, rifle and shotgun cleaning, medical equipment cleaning, medical and dental procedures, medical applications and the application of personal care products including mascara and the like. Twisted in wire brushes are also known as spiral, tube flue, bottle, pipe, boiler or power brushes, and are generally comprised of a plurality of bristles held and secured by a pair of twisted metal wires which form the core of the brush. The bristles are often formed from some type of acrylic fiber and extend radially from the core or longitudinal axis of the brush, generally resulting in a roughly cylindrical appearance. It will be readily appreciated, however, that the bristles may be formed from any suitable material including metal, such as stainless steel, brass or bronze, nylon, Teflon, polypropylene, horse or hog hair, depending on the specific use. Moreover, depending on the specification application, the ends of the brush can also vary. For example, a brush may have a rough-cut tip, a rounded tip or a bristled or fan tip, and can have a long end or handle, a short end, or a finished end having various configurations such as a ring or loop.

During the manufacturing of known brushes, the core of the brush, i.e., the twisted wire, is often cut at a distal or bristle end thereof, opposite the handle end. This cutting may leave a sharp, uneven and unfinished end. Known twisted in wire brushes may also employ a continuous end where the wire is doubled back on itself prior to twisting, as shown in prior art FIGS. 1A and 1B. The subsequent twisting to secure the bristles often leaves this continuous end (opposite the unfinished end) with rough, sharp and uneven surfaces and edges as well. This is highly undesirable in applications as discussed in detail below, where a smooth and frictionless surface is needed at the end of the brush so as to be less prone to scratch, scar or damage sensitive cleaning surfaces.

As alluded to above, twisted in wire brushes are used in many applications where an unfinished or uneven end of a brush would cause scratching or other damage. For example, such twisted wire brushes have particular application in the medical field where they are used for, among other things, cleaning the inner surfaces of catheters, arthroscopic devices, cameras, etc. Moreover, specialized brushes have been known to be used directly on or in soft and delicate tissues or cavities such as blood vessels. Accordingly, there is a need to have a finished tip on twisted in wire brushed so that a smooth and frictionless surface is presented to the interior of the vessel or cavity to be cleaned.

In view of this need, there exist several different known technologies and methods which are used to form rounded or smooth ends on twisted wire brushes in an attempt to prevent the ends of the wire core from scratching or otherwise damaging the inner walls of a vessel. One such method involves press-fitting or hand-crimping a small metal cap on the end of the brush to form a smooth and rounded tip. This process, however, is quite labor-intensive and time consuming, resulting in high labor and production costs. In addition, this method often results in inconsistent tip orientation, i.e., the metal caps are often improperly seated on the end of the brush. This increases the chance that the caps will be dislodged or displaced, which can itself create an uneven surface or expose the unfinished end of the brush, thereby resulting in scratching or damage to the interior surface of the cavity being cleaned. Moreover, this method of forming a smooth tip may result in inconsistent core wire adhesion and only allows for limited dimensional options.

Another known method of providing a smooth end on a twisted wire brush involves dipping the end of the brush into a vat of plastic or acrylic and then exposing the tip to visible or ultraviolet light to cure the plastic or acrylic. Such process results in the formation of a protective plastic or acrylic tip on the end of the brush. This method, however, often results in a rough surface texture and inconsistent tip dimensions due to both the viscosity of the plastic or acrylic used, and the time it takes for such plastic or acrylic to cure. Such rough tips are highly undesirable for use in applications where a smooth surface is needed to prevent damage to soft and sensitive vessel walls that may be prone to scratching or other damage. Moreover, even when employing this method, it is possible that the wire core section may protrude through the plastic tip during use, thereby exposing a sharp and unfinished end of the core wire section to such sensitive surfaces. These plastic or acrylic tips are also prone to dislodgment, which can result in exposure of the unfinished core wire section. Additionally, manufacturing time may be greatly increased due to extended curing times, and hazardous fumes may result from the dipping and curing process. Light curing the tips also involves semi-automatic or manual processes that may be time consuming and may result in increased labor and production costs. Moreover, as will be readily appreciated, in many applications, it is desirable to color code the tips of the brushes so as to identify the brush by type, size or use. The acrylic/plastic tip method, however, only allows for limited/inconsistent tip color options.

Insert molding is yet another known method for forming a rounded tip on the end of a brush, and involves placing the end of the brush into a mold and then injecting plastic into the mold. When the plastic hardens, the brush end is removed from the mold, producing a hardened, rounded plastic cap on the end of the brush. This method, likewise, is not without its drawbacks. Due to the high cost of mold making, it is impractical for small production runs. In addition, this process may result in core wire protrusion through the plastic tip, either from the molding process or through forces associated with cleaning. In addition, the protective tip may be inadvertently dislodged from the wire core during use, resulting in exposure of the sharp end of the core wire and potential damage to interior vessel walls. This method also does not allow for many variations in tip sizes and may result in inconsistent tip orientation. Such an inconsistent or angled tip orientation may itself cause damage to the surface to be cleaned or may cause the tip to be jarred loose during cleaning, resulting in exposure of the core wire.

Fan-tip twisted in wire brushes are another attempt to provide a protective surface on the brush end. This type of brush features "fanned" bristles on the brush end in attempt to shield the surface to be cleaned from the end of the brush. Fan-tip twisted in wire brushes, however, are less commercially attractive, have limited fan tip dimensions, and have increased production costs. In addition, during use, depending on the interaction between the bristles and the surface being cleaned, the core wire may still be exposed through the fan tip, thereby potentially causing damage to any sensitive surface.

Another inherent problem with twisted in wire brushes in general is their tendency to unravel when used in applications such as medical applications and gun cleaning where a reasonable force is necessary to effectuate cleaning, deburring, etc. In such applications, the forces generated by the cleaning motion will sometimes cause the twisted wire core to come unraveled and the bristles to become dislodged. This may cause exposure of the core wires, making the vessel more prone to scratching and other damage, and also may result in the leaving of undesirable debris, e.g., bristles or caps, within the vessel. There is therefore a need to increase the structural strength of such brushes so as to prevent unraveling in applications where a reasonable force is needed to effectuate cleaning, deburring, lubricating, etc.

In view of the problems associated with known techniques and methods for forming a rounded or smooth tip on the ends of twisted wire brushes, there is a need for an improved brush and method for forming a smooth and rounded tip on the end thereof so as to prevent unintended scarring, scratching or damage to sensitive surfaces.

SUMMARY OF THE INVENTION

In view of the foregoing, it is an object of the present invention to provide a brush having a protective tip.

It is another object of the present invention to provide a brush capable of cleaning the interior surface of a vessel without scratching or otherwise damaging such surface.

It is another object of the present invention to provide a brush that is produced in an environmentally friendly manner, without the use of acrylics or plastics.

It is another object of the present invention to provide a brush for cleaning the interior surface of a vessel having a protective tip that will not trap contaminants on its surface.

It is another object of the present invention to provide a brush having a protective tip that is less prone to dislodge from brush during use.

It is another object of the present invention to provide a brush having a protective tip that has less surface friction than known tip surfaces.

It is another object of the present invention to provide a twisted in wire brush having an increased structural strength so as to prevent unraveling of the brush or bristles in certain applications where a reasonable force is needed.

It is yet another object of the present invention to provide a method of forming a protective tip on a brush that will be cost-effective in both large and small production runs.

It is yet another object of the present invention to provide a method of forming a protective tip on a brush without the need to modify the existing technology used to manufacture such brushes, thereby adding little or no additional cost to the fabrication process.

It is yet another object of the present invention to provide a method of forming a protective tip on a brush that adds minimal time and cost to the production process.

It is yet another object of the present invention to provide an apparatus for forming a protective tip on the end of a wire brush.

It is yet another object of the present invention to provide an apparatus for forming a protective tip on the end of a wire brush without subjecting the bristles of the brush to excess heat.

It is therefore a general object of the present invention to provide a brush having a protective tip. This protective tip is smooth and rounded so as to prevent scratching or damage to sensitive and delicate interior surfaces of vessels to be cleaned. The protective tip also increases the structural strength of the core wire so as to prevent unraveling of the core and bristles in certain applications where a reasonable force is needed to effect cleaning, lubricating, etc.

It is also a general object of the present invention to provide a method of forming a protective tip on a brush, which generally comprises the step of manufacturing a brush by a known process and further comprising the step of holding the brush adjacent to, or in contact with, an electrode, laser or other heat generating assembly and "melting" a pre-constructed core wire section of the brush into an integral, smooth and inseparable protective tip. This section, once fused is unable to be separated from the brush core, thus reducing the risk of cleaning surface damage.

It is further a general object of the present invention to provide an apparatus for forming a protective tip on the end of a wire brush that includes a means for holding the brush relevant to an electrode or laser and a heat shield to prevent the presentation of any excess heat to the brush bristles.

BRIEF DESCRIPTION OF THE DRAWINGS

The present invention will be better understood from reading the following description of non-limiting embodiments, with reference to the attached drawings, wherein below.

DETAILED DESCRIPTION OF THE PREFERRED EMBODIMENTS

The present invention is directed to a cleaning device, more specifically a brush, having a protective tip that is less prone to scratch, scar or damage sensitive cleaning surfaces, and further to a method and apparatus for making the same. The brush is especially adapted to be used for cleaning the interior surfaces of vessels wherein an unfinished end of a brush may cause damage to such interior surfaces, such as in medical applications, for example, the cleaning of catheters, arthroscopic devices, cameras, etc., and for use in cleaning pistols, rifles and shotguns.

Figure 3:
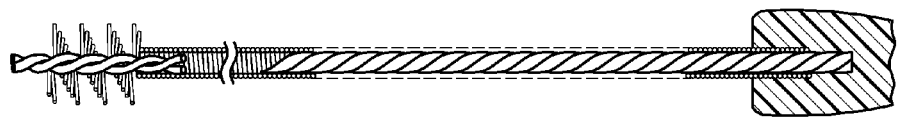
FIG. 3 is a side plan view of a prior art twisted in wire brush having an alternative configuration.
Figure 4A:
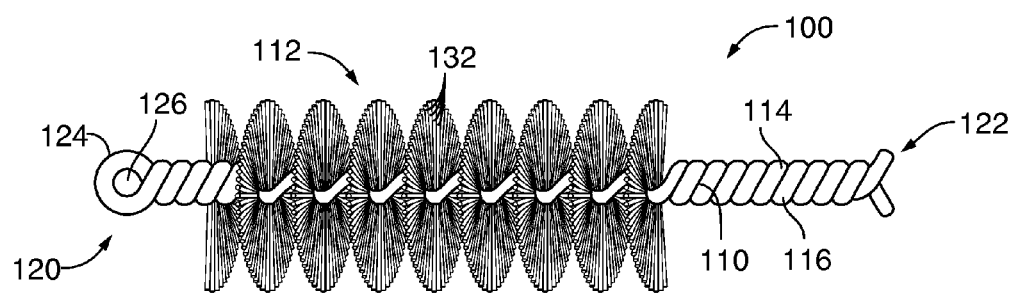
FIG. 4A is a side plan view of a continuous end type cleaning apparatus having an unfinished end in accordance with one embodiment of the present invention.
Figure 4B:
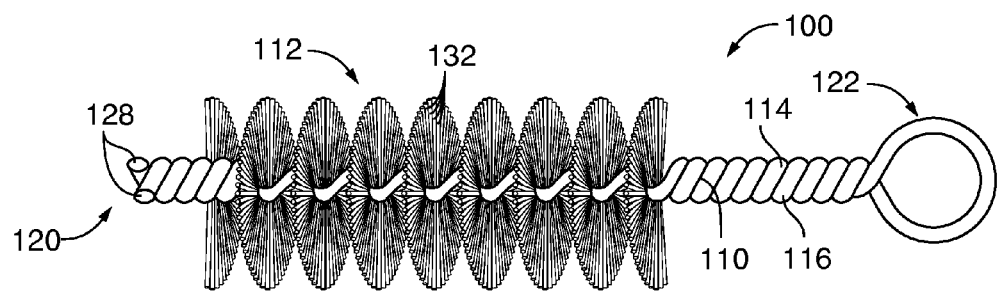
FIG. 4B is a side plan view of a broken nose type cleaning apparatus having an unfinished end in accordance with one embodiment of the present invention.

As discussed above, FIGS. 1A-3 show various configurations of prior art twisted in wire brushes at different points of the fabrication process. FIGS. 4A and 4B show two different configurations of twisted in wire brushes prior to forming the inventive protective tip, as discussed in detail below.

Figure 1A:
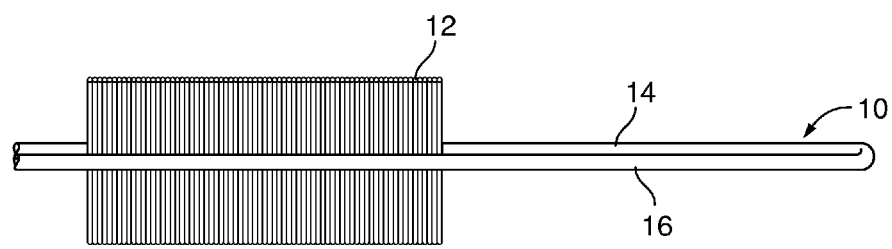
FIG. 1A is a side plan view of a prior art twisted in wire brush representative of a known cleaning apparatus prior to fabrication, and showing the placement of the bristles.
Figure 1B:
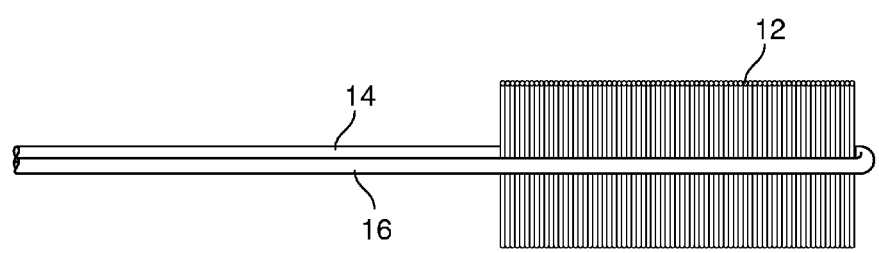
FIG. 1B is a side plan view of a prior art twisted in wire brush representative of a known cleaning apparatus prior to fabrication, and showing an alternative placement of the bristles.
Figure 2A:
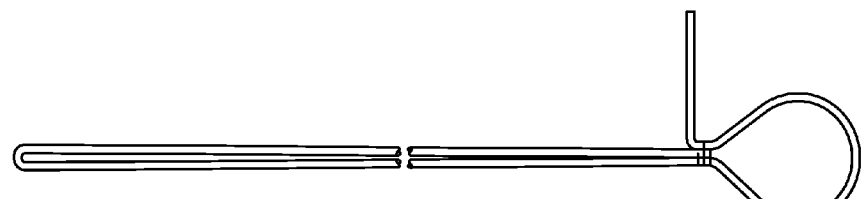
FIG. 2A is a side plan view of the wire core of a prior art twisted in wire brush according to a known configuration and prior to twisting/fabrication.
Figure 2B:
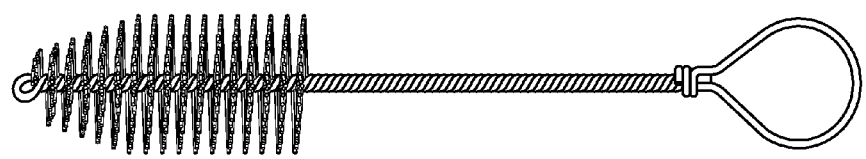
FIG. 2B is a side plan view of the prior art twisted in wire brush of FIG. 2A after insertion of a bristle block and twisting/fabrication of the core has been completed.

The brush may be fabricated in the customary manner by using a pliable metallic wire, reversibly folded back upon itself. A plurality of bristles of predetermined length are placed between the two coextensive leg portions of the wire, as shown in FIGS. 1A and 1B. The wire is then twisted to form the core of helical configuration, which grips the bristles at the midpoint of their length, causing the filaments to be crimped and folded in half. The outer tips of the bristles define a roughly cylindrical shape of predetermined diameter, or a conical shape. The bristles may be further trimmed to arrive at various additional shapes, such as the configuration shown in FIG. 2B. While this is an exemplary method of forming a cleaning apparatus, and more particularly a twisted in wire brush, it will be readily appreciated that any fabrication process or method for forming twisted in wire brushes known in the art may be employed, without departing from the scope of the present invention.

For example, it will be readily appreciated that a plurality of wires may be used in place of the single wire described above. In such a situation, the plurality of wires may be placed adjacent one another, a plurality of bristles placed between the wires, and the wires twisted together to form a core of helical configuration and to anchor the bristles in place. A brush produced by this method is shown in FIG. 3. Other methods and configurations of forming wire brushes and twisted in wire brushes are known in the art and may be incorporated in the current design without departing from the scope of the present invention.

Whether the brush is constructed from a single wire folded back on itself, or a plurality of wires, the distal or bristle end of the brush adjacent the bristle block or head portion is exposed and uncovered, which, if used in cleaning sensitive or soft surfaces, may damage or scratch such surfaces. As alluded to above, the brush may also be either of the "continuous end" type, such as that shown in FIG. 4A, where the bristle block is closest to the folded-over point of the wire core, or the "broken nose" type, such as that shown in FIG. 4B, where the bristle block is closest to the unfinished wire ends. In the case of a continuous end brush, sharp edges 124 may still be present as a result of the tight twisting of the wire. In addition, such continuous end brushes may have a void 126 or depression at the bristle end 120 thereof that is susceptible to trapping contaminants that can then be undesirably introduced in the vessel to be cleaned. The present invention is therefore equally applicable to continuous end brushes, such as shown in FIG. 4A, and broken nose brushes, such as shown in FIG. 4B.

As noted above, FIGS. 4A and 4B show a cleaning apparatus 100 of the present invention prior to the forming of the protective tip. As can be seen from FIG. 4B, the two coextensive leg portions 114,116 of the twisted wire core 110 of a broken nose brush may have very sharp and uneven end surfaces 128 at the bristle end 120 thereof. Moreover, even with continuous end brushes, the bristle end may still have sharp and uneven edges 124 and/or a contaminant trapping void 126 at the bristle end 120 thereof as a result of the tight twisting of the coextensive leg portions, as shown in FIG. 4A.

Figure 5:
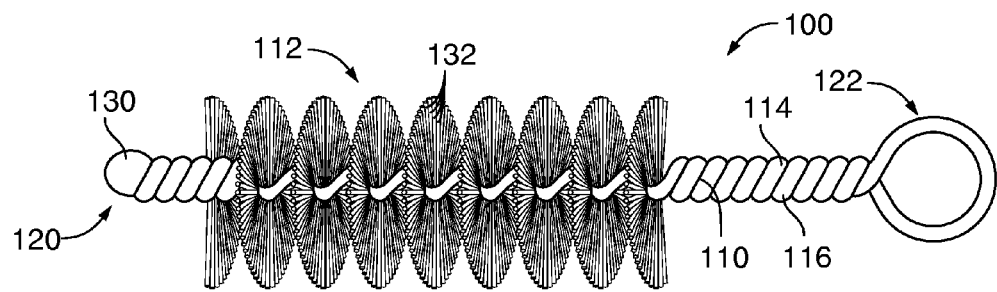
FIG. 5 is a side plan view of the cleaning apparatus of FIG. 4B and having a finished end in accordance with one embodiment of the present invention.

As shown in FIG. 5, the present invention, therefore, contemplates a cleaning apparatus 100, more specifically a twisted in wire metal brush, having a helical metallic wire core 110, a bristle block or head portion 112 formed from a plurality of discrete bristles 132, a handle fitted or formed on the terminal end or handle end 122 of the twisted wire core 110, and a protective tip 130 on the distal or bristle end 120 of the twisted wire core 110. The helical metallic wire core 110 is made up of at least two coextensive leg portions 114,116 which are twisted around each other and which anchor the bristle block. The metallic wire core may be comprised of nickel alloys, titanium alloys, stainless steel alloys, carbon steel alloys, cobalt alloys or aluminum alloys, although other metals or metal alloys may be used without departing from the scope of the present invention.

As best seen in FIG. 5, the cleaning apparatus of the protective tip 130 formed on the bristle end 120 of the brush prevents the brush from scratching, scarring or damaging sensitive cleaning surfaces, as discussed herein. This protective tip 130 is formed on the bristle end 120 of the brush, after the twisting of the core 110 to anchor the bristle block 112, in a post-production process.

To form a smooth and substantially rounded surface on the bristle end 120 of the cleaning apparatus 100, the present invention uses high-energy fusion welding to "melt" the bristle end 120 of the brush. In the case of a "broken nose" brush, welding is used to melt the end surfaces 128 of the coextensive leg portions 114, 116 of the pre-constructed core wire section 110 of the cleaning apparatus 100 into a consistent, smooth and inseparable protective tip 130. In the case of a "continuous end" brush, welding the bristle end 120 also melts and eliminates any sharp or uneven edges 124 of the cleaning apparatus 100, and likewise forms a consistent, smooth and inseparable tip 130. In addition, melting of the bristle end 120 also eliminates any contaminant trapping voids 126 that may be present. Once fused, the coextensive leg portion 114, 116 are unable to be separated from one another, and the tip 130 is also inseparable from the cleaning apparatus 100, thus reducing the risk of cleaning surface damage. As will be readily appreciated, welding of the bristled end 120 of the brush results in a metallurgical bond between the tip 130 and the core wire section 110 of the brush. Importantly, no chemical curing agents are used to form the tip, which makes the present invention especially well suited for use in medical applications.

Specific welding technologies such as Laser, Gas Tungsten Arc Welding (GTAW), Plasma Arc Welding and Electron Beam Welding may be used to melt the bristle end 120 to form the protective tip 130. In particular, the preferred parameter range is 0.001 Milliamps to 200 Amps for Gas Tungsten Arc Welding, 15 Kv-200 Kv for Electron Beam Welding and 1 Amp-200 Amps for Plasma Arc Welding, although other parameters may be used. For Laser technology, near ultra violet and/or near infra red laser sources are preferred, although other wavelengths may be used to achieve the objects of the present invention.

The welding or "melting" of the bristle end of the core wire section 110 allows for the formation of different surface geometries depending upon the welding parameters, including spherical and variations thereof. The melted or welded protective tip 130 also guarantees a smooth, clean surface that will not trap contaminants on its surface. In addition, the surface friction of the melted or welded tip can be significantly less than that of plastic-dipped tips, which is important in certain medical applications. Moreover, a further benefit of the integrally formed homogeneous tip 130 is that it allows for passivation of the brush materials, especially in the case a brush having a stainless steel or stainless steel alloy core.

It is a further advantage of the present invention that the protective tip, once formed, is incapable of being separated from the wire core, as the core and protective tip is a single welded piece, i.e., the core wire section 110 and the protective tip 130 are homogeneous. As discussed herein, prior art cleaning brushes often employ separate element tips, either of plastic or metal, that can come loose from the brush when it is retracted or moved within the cavity, which, in turn, exposes the core wire making the surface susceptible to damage from the unprotected end of the brush. Moreover, it will be readily appreciated that one of the advantages of using welding, melting or joining technology in lieu of plastic tips is that plastic tips require the use of a large and expensive mold apparatus to form such tips. Consequently, the use of plastic tips is only economically viable with very large production runs, otherwise the high cost of the injection mold would not be justified. In stark contrast to known methods, the forming of the protective tip 130 of the present invention is fast, cost-effective and adds very little time and expense to the existing fabrication process.

A further advantage of the melted protective tip formed on the brush of the present invention is that such tip increases the structural strength of the brush itself, which aids substantially in ensuring that the leg portions 114,116 do not become unraveled. This is a problem in certain applications, such as medical applications and gun cleaning, where a reasonable force is needed to effect cleaning, lubricating, deburring, etc. Moreover, the protective tip may be formed by the method and apparatus of the present invention, as discussed below, irrespective of differing diameters, lengths and materials of the core wire section 110.

As alluded to above, it will be readily appreciated that the existing technology used to manufacture twisted in wire brushes need not be modified in order to form the additional protective tip. Therefore, there is minimal additional cost associated with the fabrication of the cleaning apparatus according to the present invention. As noted above, the protective tip 130 is formed after the anchoring of the bristle block within the core wire section 110, in a post-production process.

Importantly, and in contrast to known brushes and methods for forming protective tips, the tip of the present invention is formed of the same material as the core wire of the brush, from the existing metal of the core wire at the bristle end 120 of the brush. As such, the present invention is advantageous in that there is no need to seek approval for the composition of the tip material for Food and Drug Administrative (FDA) purposes, as the customary metals and alloys comprising the core wire section 110 have already been approved for use in most cases. In particular, the biocompatibility of the protective tip 130 of the present invention is the same as the core wire section 110 of the brush. In addition, due to the homogeneity of the protective tip 130 and the core wire section 110, the wear resistance of the protective tip 130 and the core wire section 110 are substantially identical.

Figure 6:
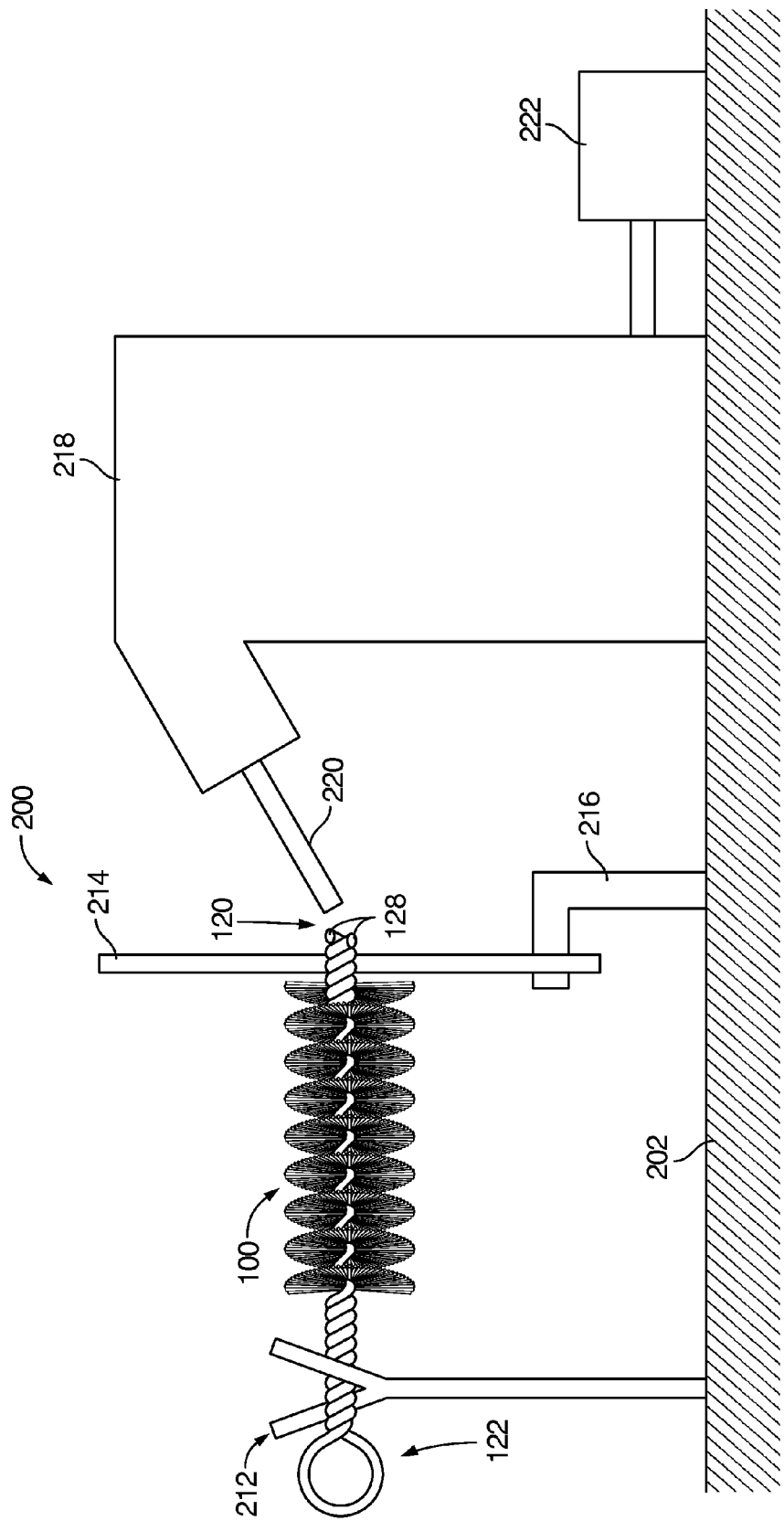
FIG. 6 is a side plan view of an apparatus for forming a protective tip on the end of a twisted wire brush in accordance with one embodiment of the present invention.

According to another embodiment of the present invention, an apparatus 200 is provided which allows the individual brush to be held adjacent to an electrode, laser or other high energy source and which has a shield to prevent the presentation of any excess heat to the bristles. FIG. 6 shows one possible configuration of the apparatus for forming a protective tip on the bristle end 120 of a cleaning apparatus 100 according to one embodiment of the present invention.

The apparatus 200 comprises a means 212 for holding, supporting, and/or clamping the cleaning apparatus 100 in place. In a preferred embodiment, means 212 grips or supports the cleaning apparatus 100 about the core wire section 110 adjacent the handle end 122. The means 212 may be a table or other surface, a vice, cantilever support, or the like, so long as the apparatus 100 is held statically in place. A cantilever support base in combination with an anti-deflection support base may also be used to further restrain the cleaning apparatus 100 for forming the protective tip 130. The anti-deflection support base prevents the bristle end 120 of the brush from developing deflections during forming of the tip 130.

With particular respect to the support and protective tip forming apparatus, the bristle end 120 is positioned through an aperture or cutout section of a heat shield 214. The heat shield may be supported by a shield support 216 or any other means known in the art. The heat shield may be made of any material so long as it is sufficient to protect the bristle block 112 from excess heat that may result in the deformation of the bristles 132 or compromise the integrity of the bristles 132. The apparatus 200 further comprises a welding machine or heat source 218 connected to a power supply 222, and includes a welding/melting tip 220 protruding therefrom that is capable of melting the end surfaces 128, sharp edges 124 and/or void 126 of the core wire section 110 of the cleaning apparatus into a smooth and substantially round ball.

It will be readily appreciated that numerous other configurations for an apparatus for forming a protective tip on a cleaning apparatus are possible without departing from the scope of the present invention. As such, any configuration of the means for holding, heat shield and heat source may be used in combination to achieve the objects of the present invention. In addition, any known means for melting or welding metal may be used as a heat source, such as Laser/Gas Tungsten Arc Welding to (GTAW)/Plasma Arc Welding and Electron Beam welding technology, to achieve the objects of the present invention, as discussed above.

Moreover, in yet another embodiment of the present invention, a method is provided for forming a protective tip on a cleaning apparatus. Such method involves manufacturing a cleaning apparatus, in particular a twisted in wire brush, by a known process, as hereinbefore described. The method further comprises the steps of positioning the bristle end of the cleaning apparatus adjacent to an electrode or laser, placing a heat shield over the bristle block 112 to shield the bristles 132 from heat, and "melting" a pre-constructed core wire section 110 of the cleaning apparatus into a consistent, smooth and inseparable protective tip 130. This section, once fused is unable to be separated from the wire core, thus reducing the risk of cleaning surface damage, as hereinbefore described.

It will be readily appreciated that this process may also be repeated on the handle end 122 of the brush if such brush is formed in a manner that leaves sharp, uneven or unfinished edges on the handle end. It may be desirable to also form a protective tip on the handle end of the brush to prevent the catching of any sharp edges and the like on clothing, etc., or to prevent the lacerating or puncturing of the skin of a user.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A method of forming a protective tip on a wire brush so as to make the brush less prone to damage sensitive surfaces, said method comprising the steps of:
    providing a brush with a wire core and a plurality of bristles defining a bristle block extending radially from said core and anchored in said core;
    melting a portion of said wire core at an end thereof, by applying an energy source to said end, to form a protective tip; and
    shielding said bristle block from said energy source prior to said step of melting to prevent damage to said bristle block.

2. The method of claim 1, wherein said step of melting a portion of said wire core at an end thereof is achieved by laser beam welding.

3. The method of claim 1, wherein said step of melting a portion of said wire core at an end thereof is achieved by gas tungsten arc welding.

4. The method of claim 1, wherein said step of melting a portion of said wire core at an end thereof is achieved by plasma arc welding.

5. The method of claim 1, wherein said step of melting a portion of said wire core at an end thereof is achieved by electron beam welding.

6. A method of forming a protective tip on a twisted wire brush having a plurality of metal leg members defining a core and a plurality of bristles retained by said core, said method comprising the steps of:
    melting an end of said core by applying an energy source to said core to form said protective tip without the addition of any other quantity of material to said core; and
    shielding said bristle block from said energy source prior to said step of melting to prevent damage to said bristle block.

7. The method of claim 6, wherein:
    all of said metal leg members are homogeneous.

8. The method of claim 6, wherein said step of melting is achieved by laser beam welding.

9. The method of claim 6, wherein said step of melting is achieved by gas tungsten arc welding.

10. The method of claim 6, wherein said step of melting is achieved by plasma arc welding.

11. The method of claim 6, wherein said step of melting is achieved by electron beam welding.

12. The method of claim 6, wherein:
    said step of melting includes melting a portion of each of said leg members of said core.

13. A method of forming a protective tip on a brush having a wire core, said method comprising the steps of:
    melting a portion of said wire core at an end thereof by applying an energy source to said end to form a smooth and substantially rounded surface at said end without the addition of any other quantity of material such that said wire core and said smooth and substantially rounded surface at said end are homogeneous; and
    shielding a bristle block of said brush from said energy source prior to said step of melting.

14. The method of claim 13, wherein:
    said wire core is formed entirely from metal.

15. The method of claim 13, wherein:
    said step of melting a portion of said wire core at an end thereof is achieved by laser beam welding.

16. The method of claim 13, wherein:
    said step of melting a portion of said wire core at an end thereof is achieved by gas tungsten arc welding.

17. The method of claim 13, wherein:
    said step of melting a portion of said wire core at an end thereof is achieved by plasma arc welding.

* * * * *